United States Patent [19]
Gould et al.

[11] Patent Number: 4,810,582
[45] Date of Patent: Mar. 7, 1989

[54] HYDROPHILIC POLYURETHANE COMPOSITION

[75] Inventors: Francis E. Gould; Ellen K. Morgan, both of Princeton; Stephen D. Reduker, Somerset, all of N.J.

[73] Assignee: Tyndale Plains-Hunter Ltd., Princeton, N.J.

[21] Appl. No.: 169,936

[22] Filed: Mar. 18, 1988

Related U.S. Application Data

[62] Division of Ser. No. 797,407, Nov. 12, 1985.

[51] Int. Cl.$^4$ .............................................. B32B 27/00
[52] U.S. Cl. ................................... 428/423.1; 424/423; 424/432; 424/443; 424/445; 424/447; 424/449; 350/410; 128/348.1; 128/849; 128/833
[58] Field of Search ..................... 427/2; 424/447, 445, 424/449, 432, 423, 443; 350/410; 128/114, 132 D, 348.1

[56] References Cited

U.S. PATENT DOCUMENTS

| | | | |
|---|---|---|---|
| 3,793,241 | 2/1974 | Kyle et al. | |
| 3,876,581 | 4/1975 | Neogi | 521/62 |
| 3,928,255 | 12/1975 | Milkovich et al. | 521/62 X |
| 3,961,629 | 6/1976 | Richter et al. | 604/369 |
| 4,279,795 | 7/1981 | Yamashita et al. | 525/292 X |
| 4,576,156 | 3/1986 | Dyck et al. | 128/132 X |

FOREIGN PATENT DOCUMENTS

| | | | |
|---|---|---|---|
| 419040 | 5/1966 | Japan | 525/458 |
| 252638 | 12/1985 | Japan | 525/458 |

*Primary Examiner*—Edith Buffalow
*Attorney, Agent, or Firm*—Ratner & Prestia

[57] ABSTRACT

Water absorptive polyurethane composition, having high mechanical strength, is formed of A. about 25% to about 75% of a hydrophilic polyether polyurethane which is the reaction product of diethylene glycol and a polyoxyethylene glycol having a molecular weight of about 1000 to about 8000 with a polyisocyanate and B. about 75% to about 25% of a hydrophobic polyester polyurethane which is the reaction product of a polyfunctional polyester derived from the condensation of a polyol with a polybasic acid with a polyisocyanate.

18 Claims, No Drawings

HYDROPHILIC POLYURETHANE COMPOSITION

This application is a division of application Ser. No. 797,407, filed 11/12/85.

This invention relates to polyurethanes and in particular to hydrophilic polyether polyurethanes having improved mechanical properties.

Hydrophilic polyurethane polymers having high water absorptivity can be produced by reacting a polyethylene ether glycol with a polyisocyanate. However, the mechanical properties of such polyurethanes in the wet state could be further improved.

It has now been discovered that hydrophilic polyether polyurethanes having excellent mechanical properties in the wet state can be realized by blending such polymers with prescribed amounts of a hydrophobic polyester polyurethane and the provision of these hydrophilic polyurethane polymer blends together with their preparation and uses constitutes the principal object and purpose of the invention.

The hydrophilic polyurethane composition of the invention comprises by weight and on a 100% basis a blend of A. about 25% to about 75% of a hydrophilic polyether polyurethane which is the reaction product of diethylene glycol and a polyethylene ether glycol having a molecular weight of from about 1000 to about 8000 with a polyisocyanate and B. about 75% to about 25% of a hydrophobic polyester derived from the condensation of a polyol with a polybasic acid with a polyisocyanate.

Surprisingly, the polymer blend retains desirable hydrophilic surface property being essentially comparable in this respect to the hydrophilic polyether polyurethane component. Yet, at the same time, the presence of the hydrophobic polyester polyurethane results in a marked increase in the tensile strength of the polymer blend in the wet state. Typically, the increase in tensile strength becomes significant when the composition of the blend approaches 25% polyether and 75% polyester, rising to a maximum between these values and then falling back to the beginning concentration, giving rise to a bell curve. Such behavior is unexpected and as yet has not been explained. Additionally, the polymer blends exhibit good hardness, both in the dry and wet stage as measured by the Durometer A Hardness Test. A further desirable property is the reduced swelling of the blends as compared to the hydrophilic polyether polyurethane per se.

The hydrophilic polyurethane blends herein are prepared by forming a mixture of the hydrophilic polyether polyurethane and hydrophobic polyester polyurethane employing mixing techniques familiar in the art. In a typical procedure, the requisite amounts of the polyether and polyester polymers are dissolved in a solvent. The resulting solution can then be applied to a suitable substrate and after evaporation of the solvent, a film of the polymer blend is obtained. Exemplary solvents include chloroform, cyclohexanone, diethylformamide, tetrahydrofuran, dimethylsulfoxide, lower aliphatic ketones such as acetone, methylethyl ketone, lower saturated, aliphatic alcohols, for example, 1 to 4 carbon atoms and the like, including mixtures of such solvents. For casting films, the solution may contain by weight from about 5% to about 10% solids while for dipping the solids content is about 3% to about 5%.

The polymer blends may also be formed by mixing finely divided polyether and polyester polyurethanes of the invention in an extruder and extruding into the desired structure or configuration.

The hydrophilic polyether polyurethane component of the herein polyurethane is prepared by reacting a major amount of a polyoxyethylene glycol having a molecular weight of from about 1000 to about 8000 or mixtures thereof, a minor amount of diethylene glycol and a polyisocyanate. Exemplary polyoxyethylene glycols are the various commercial Carbowaxes available in a range of molecular weights from the Union Carbide Corporation. Representative Carbowaxes are PEG (CARBOWAX 1450®) and PEG (CARBOWAX 8000®) in which the numbers refer to molecular weights. The proportions in which the long-chain polyglycol and the low molecular weight diethylene glycol are present in the polyether polyurethane will determine its degree of hydrophilic character. Increasing the molecular weight of the long-chain polyethylene glycol and/or the amount thereof promotes strong hydrophilic properties to the final product. Lessened hydrophilic character results by increasing the proportion of low molecular weight glycol, that is, diethylene glycol. Generally speaking, the polyether polyurethane is proposed from about 45% to 85% of the polyoxyethylene glycol, about 2.25% to 11.0% diethylene glycol and about 15% to 40% of the polyisocyanates.

The polyisocyanate used in making the hydrophilic polyether polyurethane component of the herein polyurethane blends may be represented by R(NCO)n wherein n is greater than 1, preferably 2–4, and R is an aliphatic, alicyclic, aliphatic-alicyclic, aromatic, or aliphatic-aromatic hydrocarbon compound of from 4 to 26 carbon atoms, but more conventionally from 6 to 20 and generally from 6 to 13 carbon atoms. Representative examples of the above isocyanates are: tetramethylene diisocyanate; hexamethylene diisocyanate; trimethylhexamethylene diisocyanate; dimer acid diisocyanate; isophorone diisocyanate; diethylbenzene diisocyanate; decamethylene 1,10-diisocyanate; cyclohexylene 1,2-diisocyanate and cyclohexylene 1,4-diisocyanate and the aromatic isocyanates such as 2,4- and 2,6-tolylene diisocyanate; 4,4-diphenylmethane diisocyanate; 1,5-naphthalene diisocyanate; dianisidine diisocyanate; tolidine diisocyanate; a polymeric polyisocyanate such as neopentyl tetra isocyanate; m-xylylene diisocyanate; tetrahydronaphthalene-1,5 diisocyanate; and bis(4-isocyanatophenyl)methane.

The preferred isocyanate is methylene di(cyclohexyl isocyanate). Other but slightly less preferred diisocyanates are trimethyl hexamethylene diisocyanate and isophorone diisocyanate.

Other compounds which are useful are the isocyanate equivalents which produce the urethane linkages such as the nitrile carbonate, that is, the adiponitrile carbonate of the formula:

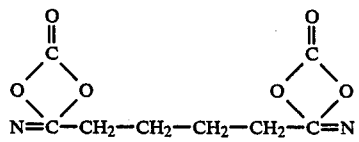

In preparing the hydrophilic polyether polyurethane component, the glycols and the polyisocyanate are reacted in the presence of known catalysts for such reaction and in this connection mention is made of tin salts and organic tin esters, for example, dibutyltin dilaurate, tertiary amines such as triethyl diamine (DABCD), N,N,N'-tetramethyl-1,3-butane diamine and other recognized catalysts for urethane reactions known in the art.

The hydrophobic polyester polyurethane components of the herein polymer blends are generally known polymer entities, the description and preparation of which are set forth in the technical and patent literature. They are obtained by condensing a polyioscyanate with a polyester resin precursor having two or more active hydrogens in the known manner of preparing polyurethane polymer. These polyesters can be regards as the esterification product of a polybasic carboxylic acid with a polyol having multiple OH groups such as polymeric diols. Examples of these diols aforesaid are polytetramethylene ether glycol, propylene oxide based polyols as well as propylene/ethylene oxide block copolymers. The polybasic acid is commonly a polycarboxylic acid of which the more familiar members include adipic acid, melletic acid, pyromellitic acid, trimellitic acid, succinic acid, itaconic acid, maleic acid, fumaric acid, mesaconic acid, azelaic acid, pimelic and the like. A polyester resin will be selected which when reacted with a polyisocyanate will yield a polyester polyurethane which exhibits little or no propensity to absorb water. A hydrophobic polyester polyurethane will normally be produced when the polymeric diol contains oxyalkylene units having 3 or more carbon atoms, for example, oxypropylene.

The hydrophilic polyurethane polyene compositions of the present invention are dimensionally stable upon repeated exposure to boiling water and have unique physical properties that are of advantage when used in the manufacture of soft contact lens.

The above described hydrophilic polyurethane polyene resin compositions are also useful as coatings, molding compounds, absorbents, controlled release agents, ion exchange resins, and in the manufacture of dialysis membranes, dentures, cannulae, contact lenses, packaging components, burn dressings, contraceptive devices, sutures, surgical implants, blood oxygenators, intrauterine devices, vascular prostheses, oral delivery systems, battery separator plates, eye bandages, corneal prostheses, antifog coatings, surgical drapes, oxygen exchange membranes, artificial finger nails, finger cots, adhesives, gas permeable membranes, and in protective and drag resistant coatings.

The invention is further illustrated by the following examples, in which the components are in parts by weight unless stated otherwise.

Preparation of Polyether Polyurethane

EXAMPLE I

A mixture of 49.0 parts of CARBOWAX 1450 ® (a polyethylene glycol having a number average molecular weight of 1450, sold by the Union Carbide Corporation, New York, N.Y. 10017) and 11.0 parts of diethylene glycol were heated to about 70+ C. with stirring until a homogeneous melt was obtained. While continuing the stirring, there was added 40.0 parts of methylene biscyclohexyl-4,4-isocyanate (a product sold as DESMODUR W ® by the Mobay Chemical Corporation, Penn Lincoln Parkway West, Pittsburgh, Pa. 15205) during which the temperature decreased. When the temperature reached about 50° C., there was added 0.15 ml of stannous octoate, (a product identified as T9 and manufactured by Metal and Thermite Company of Rahway, N.J.) and the mass allowed to exotherm to about 70° C. The mass was then poured into a polypropylene pan. During pouring, the temperature continued to rise to about 80° C. and the mass foamed. Upon finishing of the pouring operation, the pan was placed in an oven and held at 100° C. for about one hour to complete formation of the polymer.

Preparation of Polyether/Polyester Urethane Blends and Products Containing Them

The polyether polyurethane and a polyester polyurethane were dissolved in chloroform and the resulting solution used to prepare films of the polymer blend. The polyester polyurethane is obtained by the condensation of toluene diisocyanate with a polyester polyol derived from a dicarboxylic acid having 6 to 10 carbon atoms and an alkylene diol of 3 to 4 carbon atoms. Essentially equal amounts of the diisocyanate and polyester polyol are present. Films of the polymer blend were cast by applying the solvent solution aforesaid to a suitable substrate and the solvent allowed to evaporate. Films were also formed by immersing a mandrel of the requisite shape into the solvent solution, the mandrel withdrawn and the solvent allowed to evaporate. Mandrels were used to form gloves, finger cots and condoms. For casting films, the solution may contain from about 5% to 10% solids while for dipping the solution may contain 3% to 5% solids.

Blends can also be prepared from the solid polymers by mixing finely divided particles thereof in an extruder from which the polymer blend is extruded in the desired shape such as a nasal gastric tube, cannula or a film.

The polyether/polyester polyurethane blend aforesaid may be mixed with or used to encapsulate drugs or other medicament to provide controlled release thereof when placed in an aqueous or saline solution or in body fluids. The drug delivery can be of any convenient shape, for example, tablets for oral ingestion implants, suppositories, etc.

In preparing the above described polymer blends, the polyether polyurethane will be from about 25% to about 75% and the polyester polyurethane about 75% to about 25%.

EXAMPLE II

The procedure of Example I was repeated except the polyether polyurethane was made from the following components:

| | |
|---|---|
| PEG (CARBOWAX 8000 ®)* | 41.0 parts |
| Diethylene Glycol | 9.0 parts |
| DESMODUR W ® | 33.0 parts |
| Stannous Octoate (T9) | 0.15 ml |

EXAMPLE III

The procedure of Example I was repeated except the polyether polyurethane was made from the following components:

| | |
|---|---|
| PEG (CARBOWAX 8000 ®)* | 82.0 parts |
| Diethylene Glycol | 3.0 parts |
| DESMODUR W ® | 15.0 parts |

| -continued | |
|---|---|
| Dibutyl Tin Dilaurate (T$_{12}$) | 0.20 ml |

*a polyethylene glycol having a number average molecular weight of 7500-8000 and sold by the Union Carbide Corporation.

The polyether/polyester blends were immersed in water at room temperature for 24 hours, then removed and wiped with paper toweling to remove surface water. The percent water content was determined from the gain in weight of the sample. The Durometer A Hardness was measured on dry and wet samples. Tensile strength was measured on both dry and wet samples.

The polyether/polyester polyurethane of the Examples were further tested for water uptake by means of the following procedure. A sample was heat extruded at about 300° C. to form tubing, 0.25 cm in diameter and 0.058 cm wall thickness. Short lengths of the tubing samples (4 cm long) were weighed, the diameter and wall thickness were measured in the dry states. Samples were placed in water at room temperature for 24 hours, external water removed, the weight, diameter and wall thickness determined and the change in volume calculated. The percent water uptake, diameter, wall thickness and volume changes are calculated by the formula $$\frac{Xw - Xd}{Xd} \times 100$$

The water uptake of the polymer blends was essentially the same as the hydrophilic polyether polyurethane per se but with much improved mechanical strength in the state.

We claim:

1. As an article of manufacture, a shaped, three-dimensional structure formed of a water absorptive polyurethane composition comprising by weight a physical blend of A. about 25% to about 75% of a hydrophilic polyether polyurethane which is the reaction product of diethylene glycol and a polyoxyethylene glycol having a molecular weight of about 2000 to about 800 with a polyisocyanate and B. about 75% to about 25% of a hydrophobic polyester polyurethane which is the reaction product of a polyfunctional polyester derived from the condensation of a polyol with a polybasic acid with a polyisocyanate.

2. The article of manufacture in claim 1 wherein the structure is a film.

3. The article of manufacture in claim 1 wherein the structure is a burn dressing in the form of a film.

4. The article of manufacture in claim 1 wherein the structure contains a medicament.

5. The article of manufacture in claim 4 wherein the medicament is a hormone.

6. The article of manufacture in claim 4 wherein the medicament is a steroid.

7. The article of manufacture in claim 1 wherein the structure is in the form of an intrauterine device.

8. The article of manufacture in claim 7 wherein the intrauterine device contains a contraceptive composition.

9. The article of manufacture as defined in claim 1 wherein the structure is in the form of a diaphragm.

10. The article of manufacture as defined in claim 1 wherein the structure is in the form of a cannula.

11. The article of manufacture as defined in claim 10 wherein the cannula has distributed throughout its mass a medicament.

12. The article of manufacture as defined in claim 1 wherein the structure is in the form of an oral delivery system containing a pharmacologically active agent.

13. The article of manufacture as defined in claim 1 wherein the structure is in the form of a moisture-vapor permeable membrane.

14. The article of manufacture as defined in claim 1 wherein the structure has been molded.

15. The article of manufacture as defined in claim 1 wherein the structure is a contact lens.

16. The article of manufacture as defined in claim 1 wherein the structure is a corneal prosthesis.

17. The article of manufacture as defined in claim 1 wherein the structure is a surgical drape in the form of a film.

18. The article of manufacture as defined in claim 1 wherein the structure is in the form of a dialysis membrane.

* * * * *